US00PP34494P2

(12) United States Plant Patent
Cousins

(10) Patent No.: US PP34,494 P2
(45) Date of Patent: Aug. 16, 2022

(54) GRAPEVINE PLANT NAMED 'EJG ONE'

(50) Latin Name: ***Vitis vinifera* L.**
Varietal Denomination: EJG One

(71) Applicant: E. & J. Gallo Winery, Modesto, CA (US)

(72) Inventor: Peter Samuel Melugin Cousins, Modesto, CA (US)

(73) Assignee: E. & J. Gallo Winery, Modesto, CA (US)

( * ) Notice: Subject to any disclaimer, the term of this patent is extended or adjusted under 35 U.S.C. 154(b) by 0 days.

(21) Appl. No.: 17/351,070

(22) Filed: Jun. 17, 2021

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88; A01H 5/02
See application file for complete search history.

*Primary Examiner* — Keith O. Robinson
(74) *Attorney, Agent, or Firm* — Goodwin Procter LLP

(57) ABSTRACT

A new and distinct variety of grapevine plant named 'EJG One' characterized by its production of deeply colored black grapes with a distinct fruity and muscat flavor. The grapes are suitable for making wine with fruity and muscat flavors and aromas. 'EJG One' vines are fertile with spur pruning.

9 Drawing Sheets

Latin name of the genus and species of the plant claimed: The plant claimed relates to a new and distinct variety of *Vitis vinifera* L.

Variety denomination: The plant claimed shall be known as 'EJG One'.

STATEMENT REGARDING FEDERALLY SPONSORED RESEARCH OR DEVELOPMENT

The present invention is not a subject of any federally sponsored research or development.

BACKGROUND OF THE INVENTION

The new and distinct grapevine described and claimed herein originated from a wine grape breeding program. Hand pollination of the flowers of 'Aspiran Bouschet', *Vitis vinifera* L., a non-patented seed parent variety, with pollen of 'Muscat of Alexandria', *Vitis vinifera* L., a non-patented pollen parent variety, was performed in May 2012, and the resulting seeds were germinated in a greenhouse. The seedling vines were planted in a vineyard near Ripperdan, Madera County, Calif. in June 2013. The present variety of grapevine was selected as a single plant in January 2016 based on fruit yield, flavor, and composition, and was first asexually propagated by hardwood cuttings at Arroyo Grande, San Luis Obispo County, Calif. in February 2016. The resulting propagules were planted in a vineyard in April 2016 near Ripperdan, Madera County, Calif., as a replicated planting of ten vines. The resulting vines were found to be true to type, showing attributes of the original vine when observed in fruit for at least three seasons. Wine was made from grapes harvested from the ten vines and the wine was evaluated through chemical and sensory testing.

BRIEF SUMMARY OF THE INVENTION

The following description relates to the 'EJG One' grapevine when grown under normal horticultural practices near Ripperdan, Madera County, Calif. Some of the characteristics of the grapevine may vary depending upon changes in crop load and/or change of location of cultivation.

The 'EJG One' grapevine is characterized by producing medium-small dense clusters of small, deeply colored black grapes (alternatively referred to herein as "fruit" or "berries") with red flesh and a strong, distinct, pleasant fruity and muscat flavor. 'EJG One' grapes have normal development of seeds. The grapes ripen for winemaking each year in September or October. 'EJG One' flowers are perfect with functional stamens and a pistil and produce viable pollen. 'EJG One' is fertile with spur pruning. 'EJG One' grapes are suitable for wine production and the wine is positively distinguished by its deep red color, coating mouthfeel, and floral, muscat, and fruity flavors and aromas. The positive color, mouthfeel, flavor, and aroma attributes of the wine demonstrate the usefulness of 'EJG One'.

'EJG One' differs from its seed parent by producing grapes with a fruity and muscat flavor, while the seed parent produces grapes with a non-muscat flavor. 'EJG One' differs from its pollen parent by producing grapes with black skin and red flesh, while the pollen parent produces grapes that are green or yellow in color, which may be characterized as white in viticulture and/or winemaking terminology. Microsatellite (e.g., simple sequence repeat) markers were used to develop a DNA fingerprint of 'EJG One', and a comparison of the 'EJG One' DNA fingerprint to an extensive, non-public database of grapevine variety DNA fingerprints showed that the 'EJG One' DNA fingerprint was different from all the other DNA fingerprints. This observation is consistent with the origin of 'EJG One' as a distinct grapevine that arose from a seed resulting from pollination between varieties.

Commercially grown wine grape varieties that are most similar to 'EJG One' are 'Turan' (non-patented) and 'Muscat Hamburg' (non-patented). 'EJG One' differs from 'Turan' in several important ways. For example, 'EJG One' is later ripening than 'Turan', which ripens for winemaking in July or August. 'EJG One' also has larger grape clusters than 'Turan'. Further, 'Turan' shoots are strongly erect, while 'EJG One' shoots are semi-drooping. 'EJG One' differs from 'Muscat Hamburg' in that 'EJG One' grapes are deeply colored, with black skin and red flesh, while 'Muscat Hamburg' grapes are lightly colored, with pale black skin and colorless flesh. 'EJG One' grapes are smaller than 'Muscat Hamburg' grapes; however, both 'EJG One' and 'Muscat Hamburg' grapes have a muscat and fruity flavor.

BRIEF DESCRIPTION OF THE DRAWINGS

The accompanying photographs illustrate 'EJG One' in full color. The colors are as nearly true as is reasonably possible in a color representation of this type. For reference, many of the photographs include the following: a 24-color card sold by CAMERATRAX, a code number (12072240) that was used for testing 'EJG One', and gridlines in which each square is 1 cm×1 cm. The grapevines and portions thereof shown in the photographs were grown in the vicinity of Ripperdan, Madera County, Calif. The photographs were obtained during the year 2020 when the grapevines were about four (4) years old.

DETAILED BOTANICAL DESCRIPTION

Figure 1:
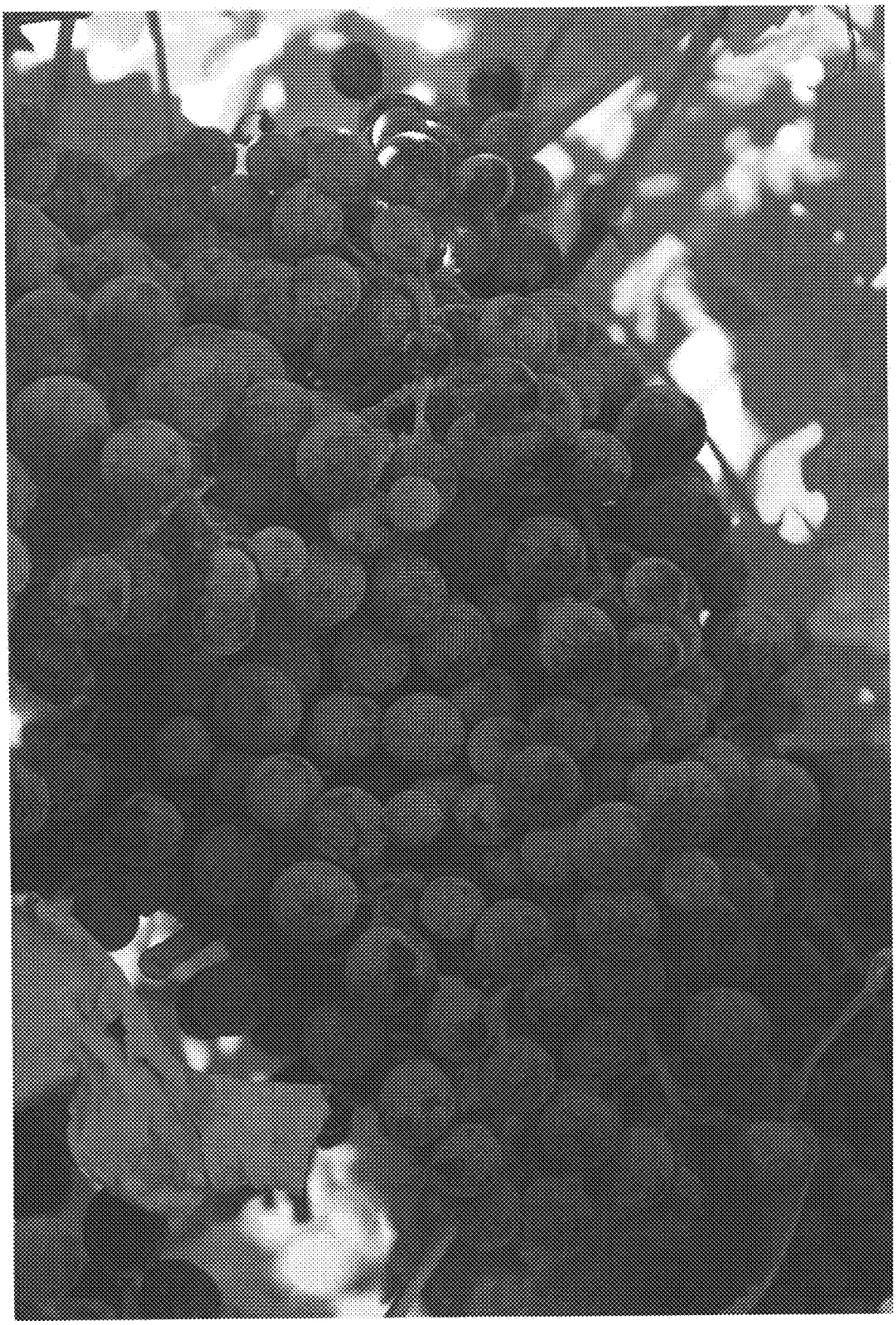
FIG. 1 includes a photograph of a grape cluster on 'EJG One' during September.
Figure 2:
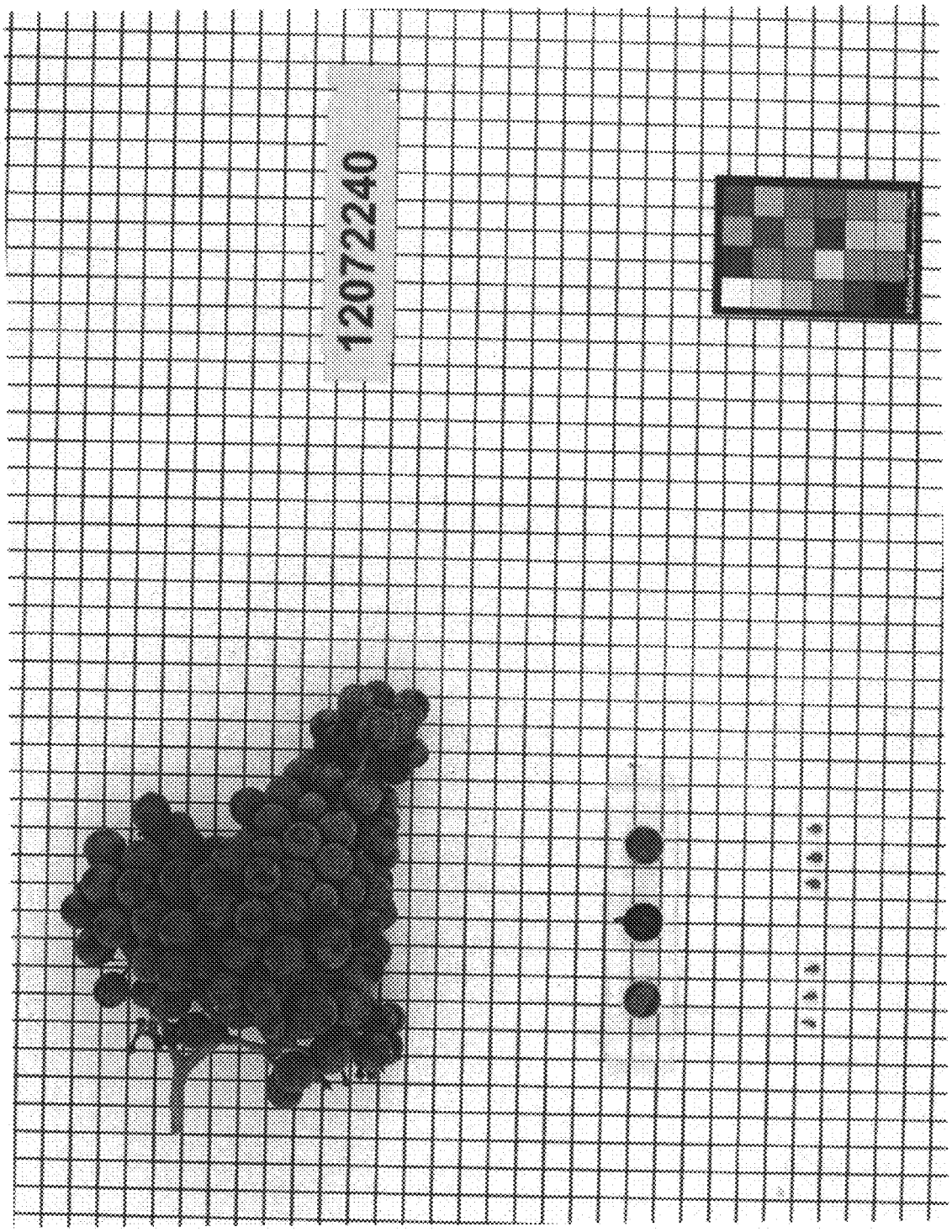
FIG. 2 includes a photograph of a grape cluster, three grapes, and six seeds during September. A grape in the middle of the three grapes has been cut in half.
Figure 3:
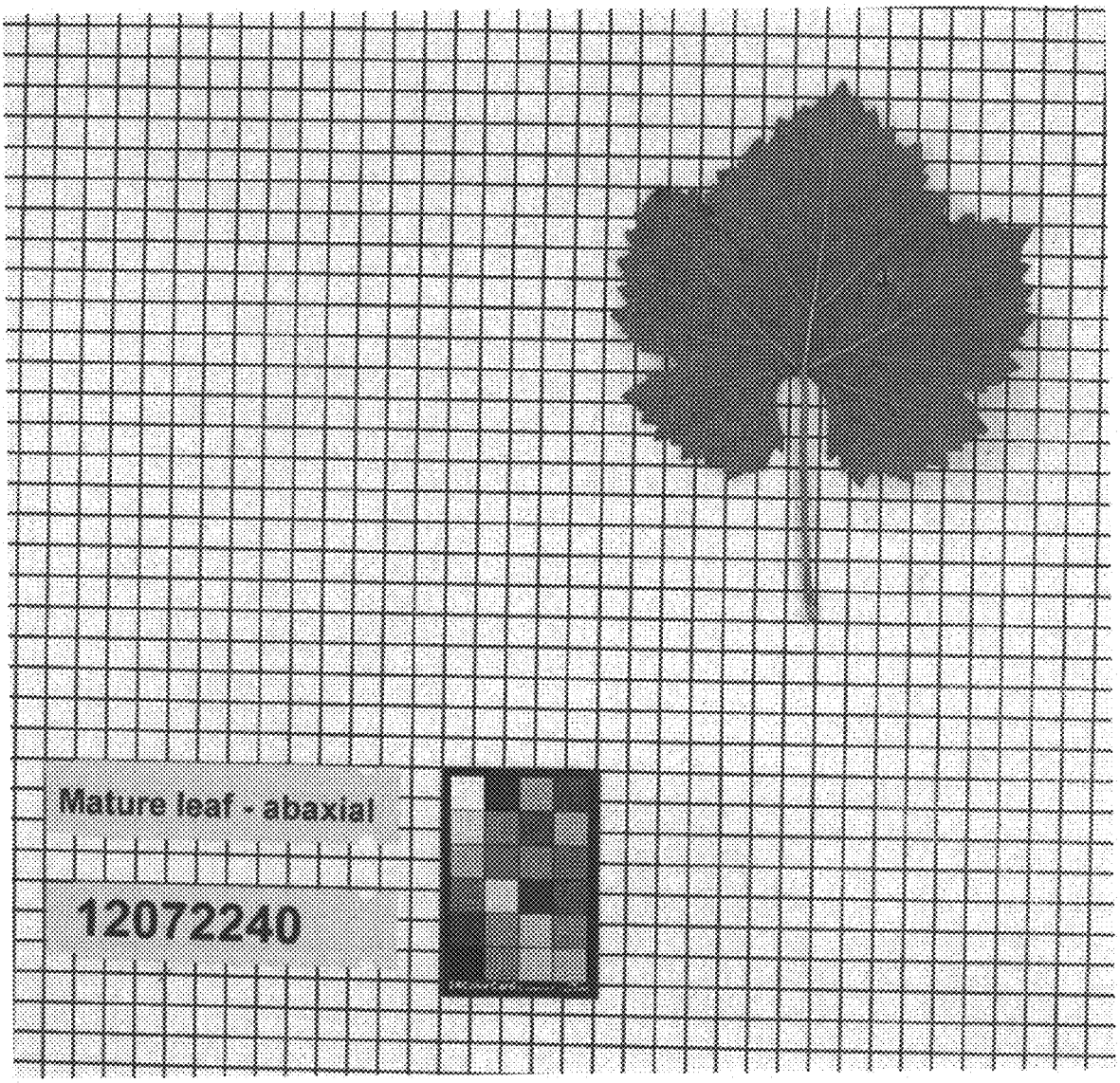
FIG. 3 includes a photograph of an abaxial surface of a mature leaf during July.
Figure 4:
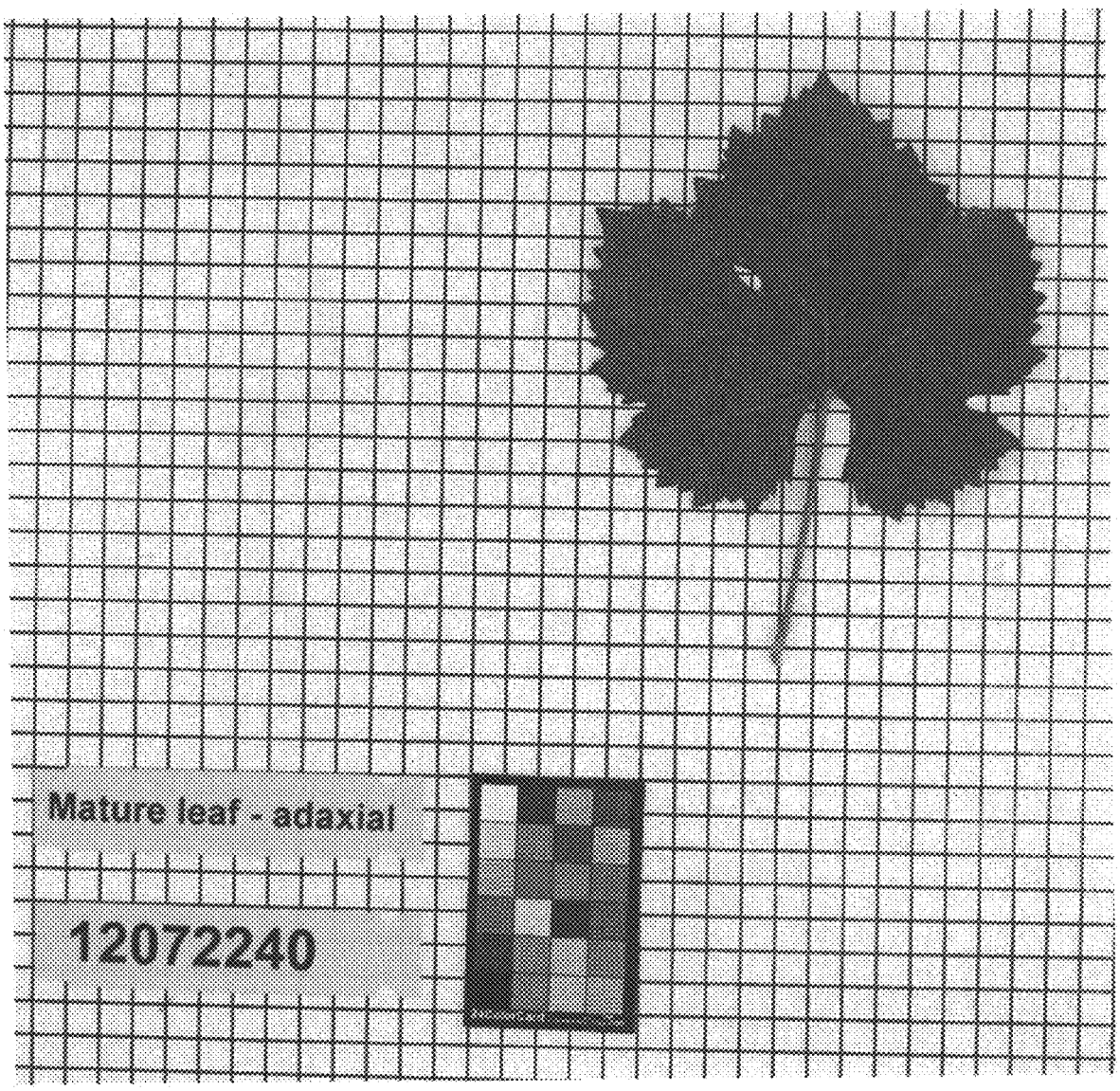
FIG. 4 includes a photograph of an adaxial surface of a mature leaf during July.
Figure 5:
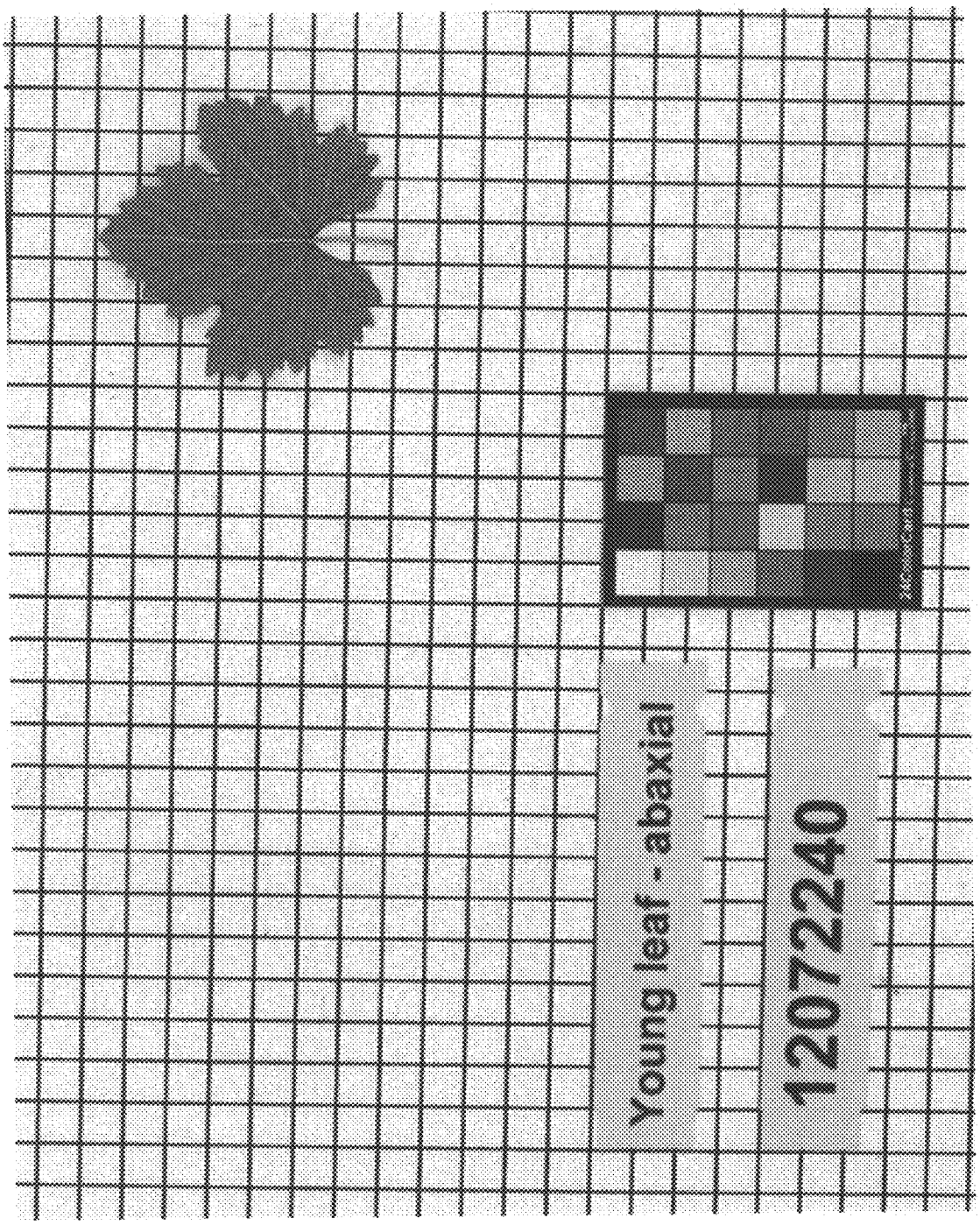
FIG. 5 includes a photograph of an abaxial surface of a young leaf during July.
Figure 6:
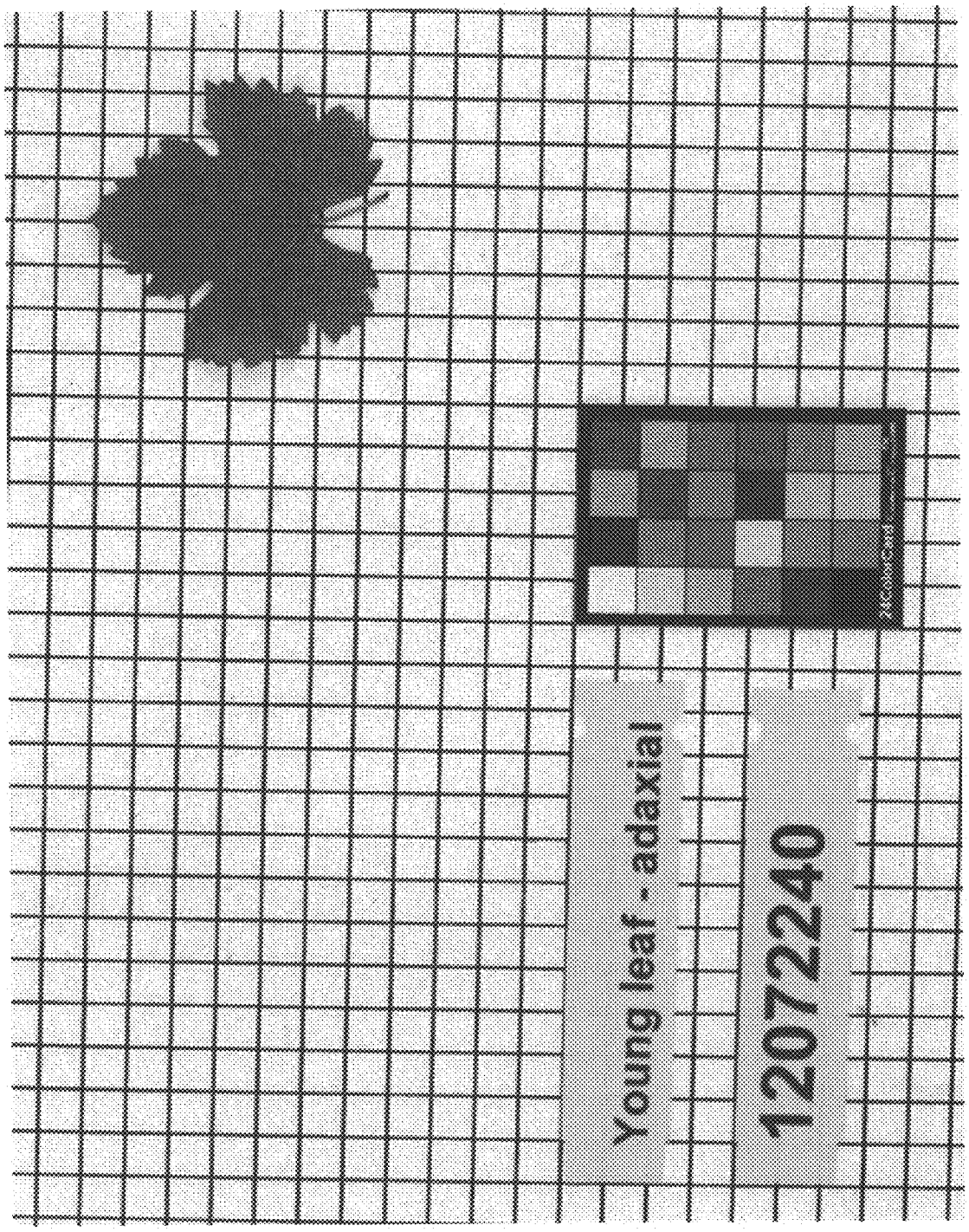
FIG. 6 includes a photograph of an adaxial surface of a young leaf during July.
Figure 7:
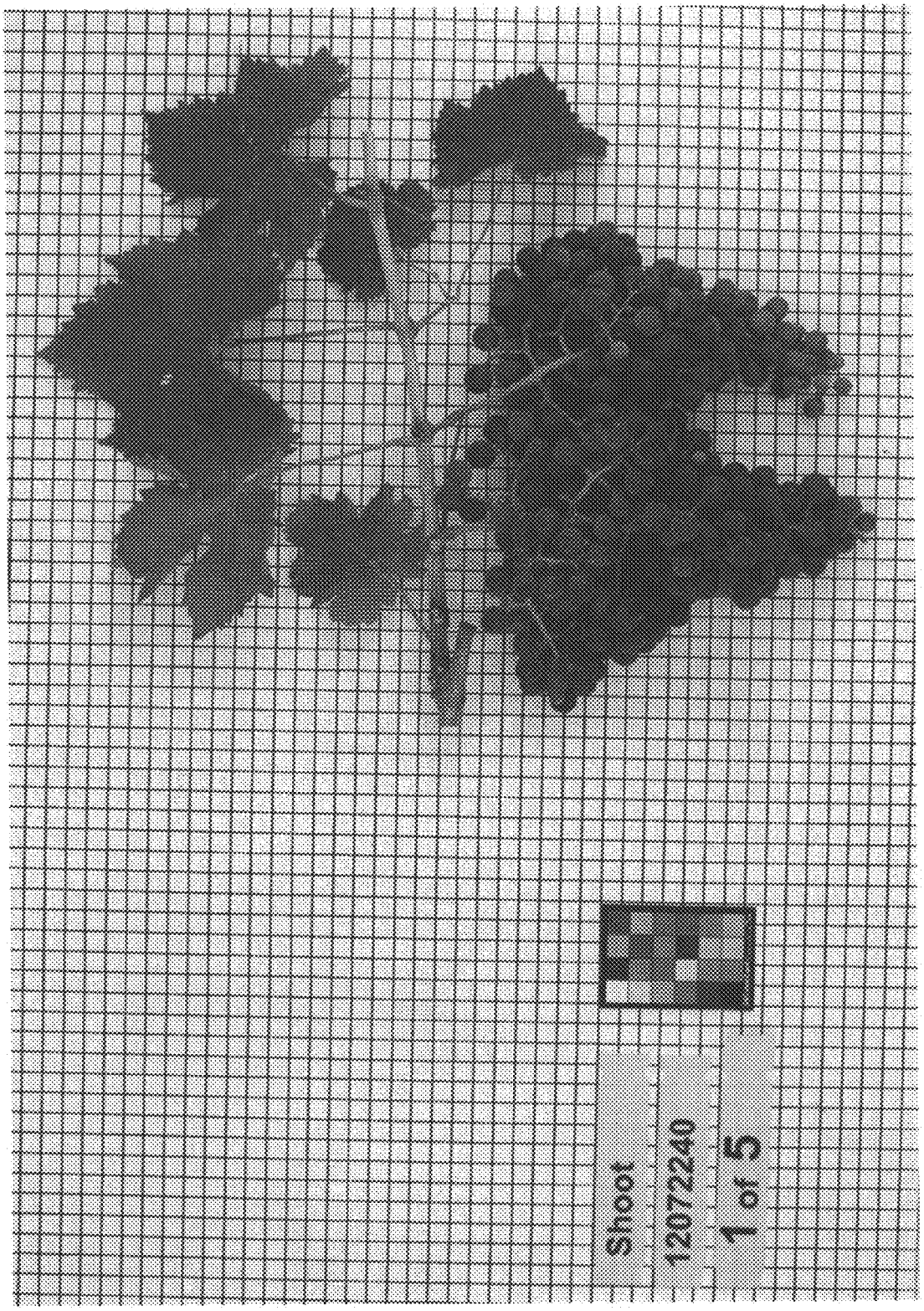
FIG. 7 includes a photograph of a shoot base during July.
Figure 8:
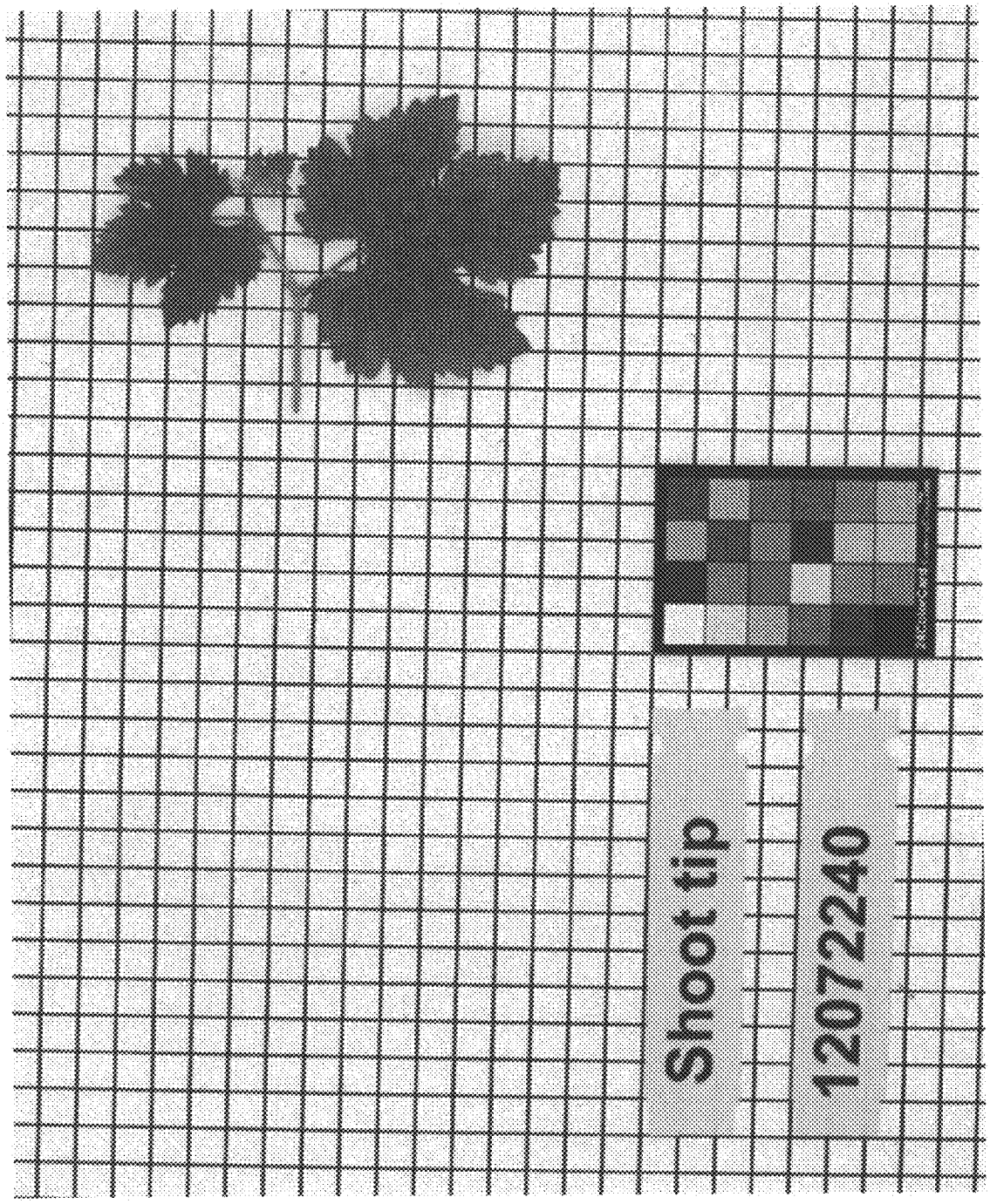
FIG. 8 includes a photograph of a shoot tip during July.
Figure 9:
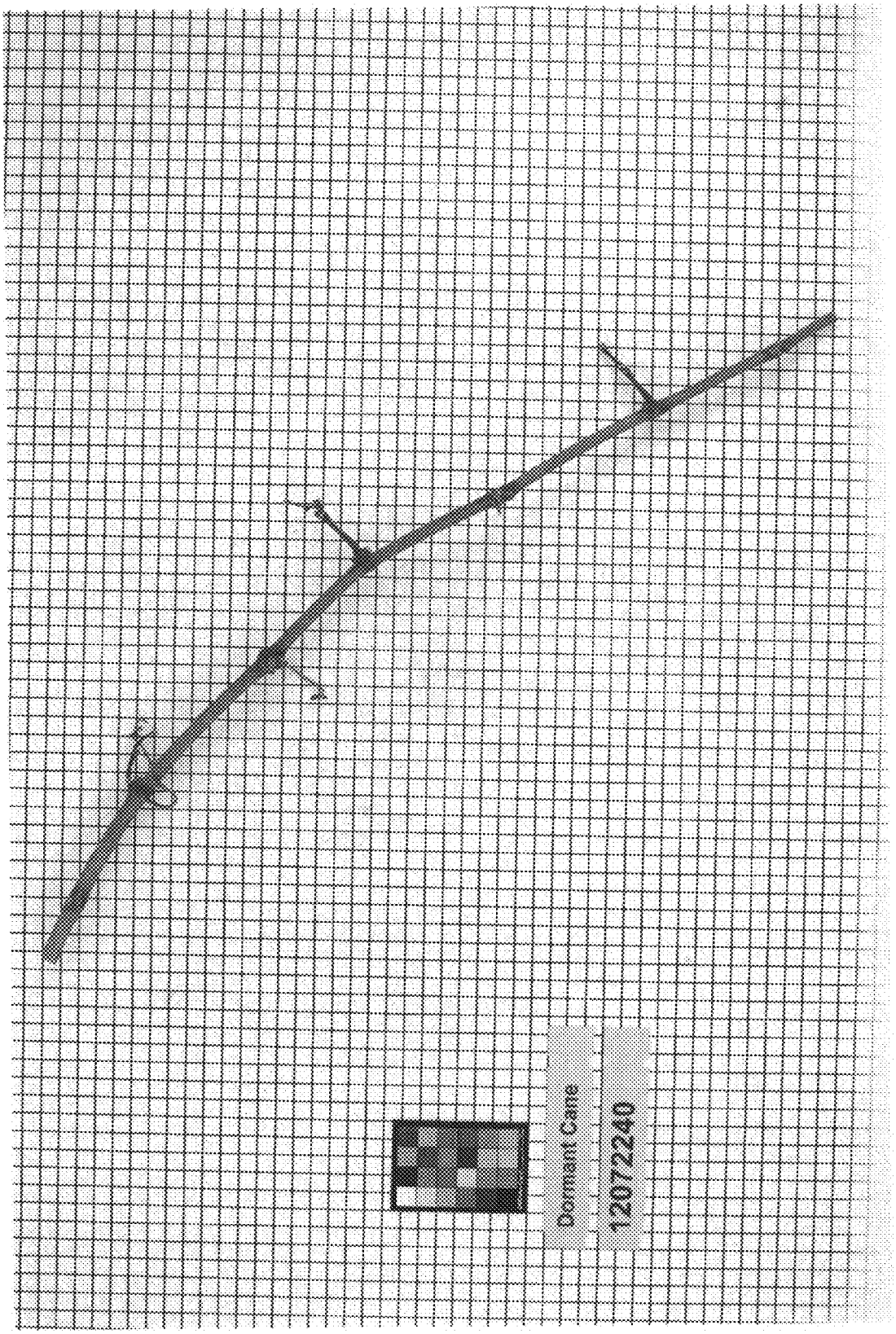
FIG. 9 includes a photograph of a dormant cane during December.

The following detailed description sets forth the distinctive characteristics of 'EJG One'. Colors refer to the designations of the Munsell Book of Color Glossy Collection, Part No. 40115B, Serial No. 55635311119, published in 2012. The descriptions pertain to grapevines grown in the vicinity of Ripperdan, Madera County, Calif. that were observed during 2020 and other years, and the descriptions are believed to apply to plants of the variety grown under similar conditions elsewhere. The vines from which the observations were made were about four (4) years old and were grown on their own roots (not grafted).

Buds:

*Bud break date.*—Mar. 23, 2020.

Cluster:

*Berries per cluster.*—328.
*Cluster density.*—Dense.
*Cluster dimensions, length.*—181 mm.
*Cluster dimensions, width.*—143.2 mm.
*Clusters per shoot.*—2.
*Peduncle length.*—34.9 mm.
*Rachis color.*—2.5GY 6/8 5R 4/8; Green-Yellow and Red.
*Weight.*—165 g.

Flower:

*Date of first bloom.*—May 5, 2020.
*Date of full bloom.*—May 18, 2020.
*Flower diameter.*—1.72 mm.
*Flower length.*—2.8 mm.
*Flowers per cluster.*—1363.
*Inflorescence diameter.*—21.2 mm.
*Inflorescence length.*—105 mm.
*Node location of first inflorescence.*—4.
*Type.*—Self-fertile hermaphrodite (perfect) with erect stamens.

Fruit:

*Attachment.*—Difficult to detach.
*Berry flesh color.*—10PB 2/1; Green-Purple-Blue Grays.
*Berry skin color.*—5PB 2/1; Green-Purple-Blue Grays.
*Berry diameter at base.*—3.3 mm.
*Berry diameter at equator.*—13.6 mm.
*Berry length.*—14.3 mm.
*Berry shape.*—Round.
*Brush length.*—4.6 mm.
*Firmness.*—Medium.
*Harvest date, day of year.*—262.
*Juiciness.*—Slightly juicy.
*Pulp texture.*—Slightly crunchy.
*Skin thickness.*—Thin.

Juice:

*Color.*—2.5R 2/2; Red.

Leaves:

*Arrangement of mature leaves (phyllotaxy).*—Alternate.
*Color of mature leaves, base abaxial.*—5GY 5/4; Green-Yellow.
*Color of mature leaves, base adaxial.*—7.5GY 3/4; Green-Yellow.
*Color of mature leaves, midpoint abaxial.*—5GY 5/4; Green-Yellow.
*Color of mature leaves, midpoint adaxial.*—7.5GY 3/4; Green-Yellow.
*Color of mature leaves, terminal abaxial.*—5GY 5/4; Green-Yellow.
*Color of mature leaves, terminal adaxial.*—7.5GY 3/4; Green-Yellow.
*Color of veins on mature leaves, abaxial surface.*—2.5GY 8/2; Green-Yellow.
*Color of veins on mature leaves, adaxial surface.*—7.5R 3/4; Red.
*Color of young leaves, base abaxial.*—10Y 8.5/2; Yellow.
*Color of young leaves, base adaxial.*—5R 3/4; Red.
*Color of young leaves, midpoint abaxial.*—10Y 8.5/2; Yellow.
*Color of young leaves, midpoint adaxial.*—5R 3/4; Red.
*Color of young leaves, terminal abaxial.*—10Y 8.5/2; Yellow.
*Color of young leaves, terminal adaxial.*—5R 3/4; Red.
*Length of mature leaves.*—149.7 mm.
*Thickness of mature leaves.*—0.29 mm.
*Width of mature leaves.*—147.4 mm.
*Leaf pubescence on young leaves, abaxial surface.*—Minimal.

*Leaf pubescence on young leaves, adaxial surface.*—Absent.
*Margin of mature leaves* (*describe*).—Serrate with large and small teeth.
*Marginal teeth height.*—4.3 mm.
*Marginal teeth width.*—5.6 mm.
*Number of lobes on mature leaves.*—4.
*Petiole sinus of mature leaves.*—Lobes half open.
*Pubescence on mature leaves, abaxial side.*—Present.
*Pubescence on mature leaves, adaxial side.*—Not present.
*Shape of mature leaves.*—Wedge.
*Surface texture of mature leaves, abaxial side.*—Smooth.
*Surface texture of mature leaves, adaxial side.*—Smooth.
*Vein color of young leaves, abaxial side.*—5YR 7/2; Yellow-Red.
*Vein color of young leaves, adaxial side.*—10Y 8/2; Yellow.
*Venation of mature leaves.*—Regular.
*Shape of teeth of mature leaves.*—Both sides straight (rectilinear).

Pedicel:
*Color.*—2.5GY 7/6; Green-Yellow.
*Diameter.*—1.1 mm.
*Length.*—6.6 mm.

Petal:
*Color.*—5GY 5/6; Green-Yellow.
*Number.*—5.
*Color of mature petioles.*—5R 3/4; Red.

Petioles:
*Color of young petioles.*—7.5R 2/6; Red.
*Length of mature petioles.*—115 mm.
*Thickness at base of mature petioles.*—4.2 mm.
*Pubescence on mature petioles.*—Absent.
*Shape of mature petioles.*—Round.

Pistil:
*Color.*—5GY 4/8; Green-Yellow.
*Length.*—2.4 mm.

Seed:
*Color.*—5R 4/2; Red.
*Length.*—5.3 mm.
*Number per berry.*—4.
*Seed development.*—Complete, producing typical hard brown seeds.
*Seeds present/absent.*—Present.
*Shape.*—Pyriform.
*Weight.*—0.01 g.
*Width.*—3.1 mm.

Shoots (current-season canes):
*Color of shoots.*—2.5GY 6/6 10R 3/6; Green-Yellow and Red.
*Length of internode above cluster.*—40 mm.
*Node color.*—7.5R 4/6; Red.
*Shoot attitude.*—Semi droop.
*Width at node bearing cluster.*—12.4 mm.
*Openness of a tip of a young shoot.*—Fully open.
*Density of prostrate hairs on a tip of a young shoot.*—Medium.

Stamen:
*Color of anther.*—2.5Y 8.5/8; Yellow.
*Color of filament.*—2.5GY 9/2; Green-Yellow.

Tendrils:
*Color of mature tendril.*—10Y 6/6; Yellow.
*Length.*—122 mm.
*Thickness at base.*—1.8 mm.
*Node location of first tendril.*—8.
*Phyllotaxy* (*pattern*).—Intermittent.
*Ramification.*—Branched.
*Texture.*—Smooth.

Trunk:
*Color.*—10YR 6/2; Yellow-Red.
*Diameter at* 30 *cm above soil level.*—133.4 mm.
*Shape.*—Round.

Vine:
*Density of foliage.*—Slightly moderate.
*Growth vigor.*—Slightly moderate.
*Size.*—Small/medium.

What is claimed is:

1. A new and distinct variety of grapevine plant named 'EJG One', substantially as illustrated and described herein.

* * * * *